United States Patent [19]

Nagano et al.

[11] 4,200,640
[45] Apr. 29, 1980

[54] NITRIC ESTER OF N-(2-HYDROXYETHYL)NICOTINAMIDE AND PHARMACEUTICAL USE

[75] Inventors: Hiroyuki Nagano, Iwatsuki; Takashi Mori, Tama; Sakae Takaku, Ageo; Isao Matsunaga, Tokyo; Tatsuo Kujirai, Ohmiya; Toshichika Ogasawara, Tokyo; Shigeru Sugano, Musashino; Minoru Shindo, Tokyo, all of Japan

[73] Assignee: Chugai Seiyaku Kabushiki Kaisha, Tokyo, Japan

[21] Appl. No.: 940,194

[22] Filed: Sep. 7, 1978

Related U.S. Application Data

[63] Continuation-in-part of Ser. No. 781,524, Mar. 25, 1977, abandoned.

[30] Foreign Application Priority Data

Apr. 2, 1976 [JP] Japan .................. 51-36101
Jul. 13, 1976 [JP] Japan .................. 51-82458
Jul. 15, 1976 [JP] Japan .................. 51-83522

[51] Int. Cl.$^2$ .................. A61K 31/455; C07D 213/81; C07D 213/82
[52] U.S. Cl. .................. 424/266; 546/316; 546/323
[58] Field of Search .................. 424/266; 546/316, 323

[56] References Cited

U.S. PATENT DOCUMENTS

| | | | |
|---|---|---|---|
| 3,036,074 | 5/1962 | Stieglitz et al. | 546/316 X |
| 3,092,634 | 6/1963 | Halpern | 546/316 |
| 3,168,438 | 2/1965 | Halpern | 546/316 X |

FOREIGN PATENT DOCUMENTS 51-1624 1/1976 Japan.

OTHER PUBLICATIONS

Yoshida et al., Mie Medical Journal, vol. 16(3), 1967, pp. 207–211.
Nauom et al., Chemical Abstracts, vol. 25(1931), 2739.

*Primary Examiner*—Richard Raymond
*Attorney, Agent, or Firm*—Browdy and Neimark

[57] ABSTRACT

A compound of the formula

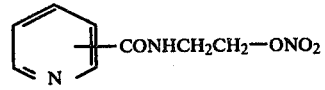

is useful for treating circulatory diseases.

17 Claims, 19 Drawing Figures

NITRIC ESTER OF N-(2-HYDROXYETHYL)NICOTINAMIDE AND PHARMACEUTICAL USE

This is a CIP of copending application Ser. No. 781,524, filed Mar. 25, 1977, now abandoned, the contents of which are hereby incorporated by reference.

This invention relates to a novel pyridine derivative, process for preparing the same and a pharmaceutical composition. More particularly, this invention relates to a pyridine derivative represented by the formula (I)

or a salt thereof; a process for preparing the same and a pharmaceutical composition containing the derivative.

Some nicotinic acid derivatives or nicotinamide derivatives have been reported in some references, for example, Japanese Patent Disclosure 1624/1976, U.S. Pat. No. 3,092,634, U.S. Pat. No. 3,168,438 and "Mie Medical Journal" Vol. 16(3), pp. 207–211, (1967).

The Japanese Patent Disclosure discloses that nicotinic ester derivatives are prepared by reacting 1-nicotinylglycerine or 1-nicotinyl-2,3-isopropylidene glycerine with fuming nitric acid, to obtain 1-nicotinyl glycerine-2,3-dinitrate and then converting the compound to its dioxane addition compound which has a coronary vasodilating action.

U.S. Pat. No. 3,092,634 and U.S. Pat. No. 3,168,438 disclose that bis-nitric ester of N,N-bis(β-hydroxyethyl) nicotinamide which has coronary vasodilating action is prepared by reacting nitric ester of diethanolamine with nicotinic acid chloride.

However, the compounds which have been reported have short term action or adverse action against blood pressure or function of heart and, thus, do not suffice as a drug to stimulate the circulatory system, for example, in the case of ischemic heart disease. Under the circumstances, the development of an ideal drug has been desired.

In "Mie Medical Journal", Vol. 16(3), pp. 207–211 (1967), 2-nicotinamido ethanol is mentioned. However, the compound is merely shown as a test compound for anti-tumor action and the Journal reported no remarkable pharmacological action.

U.S. Pat. No. 3,036,074 discloses, for the most part, compounds having a xanthine ring and said to be interesting from the point of view of the manufacture of explosives and pharmaceutical products causing an increased coronary flow. Example 8, however, shows the nitrate of the acid dinitroxydiethyl amide nicotinate rather than a xanthine ring compound. However, this compound has a very short duration of effectiveness and has other disadvantages.

After much research there has now been found a compound useful for the treatment of circulatory disease without deficiencies of the prior art.

This invention relates to a compound represented by the formula (I)

and its salts, a process for preparing the same and a pharmaceutical composition containing the above compound or its salt.

The compound of the present invention or its salt is novel and has improved activity for treating circulatory disease, such as coronary vasodilating action, antihypertensive action, antiarrhythmic action, anticoagulative action and peripheral vasodilating action, and, thus, it is useful for treating ischemic heart disease, as an antihypertensive drug, anticoagulative drug, antiarrhythmic drug, and as a peripheral vasodilator including cerebral vasodilator and renal vasodilator.

According to the present invention the compound of the formula (I) may be prepared by one of the following methods:

(1) A compound represented by the formula (II)

or its functional derivative at carboxyl group is reacted with a compound represented by the formula (III)

or its functional derivative at amino group; and (2) a compound represented by the formula (IV)

wherein $R_3$ is hydrogen, lower alkyl or hydroxy and $R_4$ is hydroxy or —CH$_2$OH is reacted with a nitrating agent.

The functional derivatives of the compound (II) at carboxyl group include, for example, acid halide, acid anhydride, active amide, active ester and the like. The derivatives which may be commonly used are acid chlorides; acid azides; acidanhydrides such as anhydrides derived from two moles of the compound (II) and anhydrides of the compound with another acid for example, dialkylphosphoric acid, phenylphosphoric acid, diphenylphosphoric acid, benzylphosphoric acid, halogenated phosphoric acid, dialkylphosphorous acid, sulfurous acid, thiosulfuric acid, sulfuric acid, alkylcarbonic acid, fatty acid such as pivalic acid, pentanoic acid, isopentanoic acid, 2-ethylbutanoic acid or trichloroacetic acid, or aromatic carboxylic acid such as benzoic acid; amides for example, amides with imidazole, 4-substituted imidazole, dimethylpyrazole, triazole or tetrazole; and esters, for example, cyanomethyl ester, 4-Nitrophenyl ester, 2,4-dinitrophenyl ester, trichlorophenyl ester, pentachlorophenyl ester, methanesulfonylphenyl ester, phenylazophenyl ester, phenylthio ester, 4-nitrophenylthio ester, p-cresylthio ester, carboxymethylthio ester, pyranyl ester, pyridyl ester, 8-quinolylthio ester and esters with N,N-dimethylhydroxylamine, 1-hydroxyl-2-(1H)-pyridone, N-hydroxysuccinimide or N-hydroxyphthalimide.

The starting compounds (III) may be used as an activated form at amino group which can be activated by the use of phosphorous trichloride, ethyl chlorophosphite, methyl chlorophosphite or the like.

The process as defined in method (1) above may be carried out by reacting, for example, a reactive derivative of the compound (II) at carboxyl group with the compound (III) to condense them at a temperature of from $-10°$ to $50°$ C., preferably $0°$–$10°$ C. for 0.5–4 hours. The solvents which may be used for this reaction include water, benzene, toluene, tetrahydrofuran, diethyl ether, dioxane, dimethyl-formamide, chloroform, methylene chloride, acetonitrile, acetone, carbon tetrachloride ethyl acetate and the like. An accelerator for the condensation reaction may be used, which includes inorganic basic substances, for example, hydroxide, carbonate or acetate of an alkali methal or alkaline earth metal, such as sodium acetate, sodium carbonate, potassium acetate, potassium carbonate, sodium hydroxide, calcium acetate, calcium carbonate; or amine compounds such as pyridine, triethylamine, dimethylaniline, picoline or the like.

The condensation reaction of the compound (II) with the compound (III) the amino group of which has been activated with phosphorous trichloride, ethyl chlorophosphite, methyl chlorophosphite or the like may be conveniently carried out at from room temperature to the reflux temperature of a solvent used for 0.5–3 hours. The solvent usually used for this invention includes a neutral solvent, such as benzene, toluene, xylene, dioxane or tetrahydrofuran; or a basic solvent such as pyridine, triethylamine, dimethylamine, dimethylaniline or picoline. In case the neutral solvent is used, it is preferable to add amine compound such as pyridine, triethylamine dimethylaniline, picoline or the like.

In another embodiment of the invention, the compound (II) may be reacted with the compound (III) in an inert solvent in the presence of an amide-formation accelerator, for example, an imide compound such as N,N'-dicyclohexylcarbodiimide, N-cyclohexyl-N'-morpholinoethylcarbodiimide, N,N'-diethylcarbodiimide or the like; an imine compound such as diphenylketene-N-cyclohexylimine, pentamethyleneketene-N-cyclohexylimine or the like; or a phosphate or phosphite such as triethyl phosphite, ethyl polyphosphate, isopropyl polyphosphate or the like at from room temperature to the reflux temperature of the solvent used for 1–5 hours. The inert solvent which may be used in this reaction includes, for example, benzene, toluene, tetrahydrofuran, chloroform, dioxane, acetonitrile and dimethylformamide.

The reaction as previously defined in Method (2) may be carried out by reacting the compound (IV) with a nitrating agent in an inert solvent such as chloroform, dichloromethane or the like at a temperature of from $-5°$ C. to room temperature for 1–3 hours. The nitrating agent which may be generally used in this reaction is fuming nitric acid, nitrile chloride or the like.

The compound (I) prepared by Method (1) or Method (2) may be converted to its organic or inorganic acid addition salt such as hydrochloride, nitrate, oxalate, p-toluenesulfonate, maleate or the like.

The object compound, pyridine derivative (I) may be formulated by a conventional way into a pharmaceutical composition in the form of tablet, granule, powder, capsule, suspension, parenteral injection, suppository or the like. For the preparation of tablet, powder, granule or capsule filled with powder or granule, the object compound may be mixed with one or more pharmaceutical carriers such as lactose, starch, mannitol, kaolin, crystaline cellulose, talc, calcium carbonate, magnesium stearate or the like. For the preparation of soft capsule filled with liquid preparation, the object compound may be dissolved in an oil. The object compound may also be suspended in an arabic gum or sucrose aqueous solution and the pH adjusted. On the other hand the object compound may be blended with mannitol to make it suitable for parenteral injection.

The pyridine derivative according to this invention may be present in any form of the pharmaceutical composition in an amount sufficient to exhibit the actions for treating or preventing circulatory disease but not to exhibit any adverse action by the administration of the composition. A unit dosage form such as a tablet or capsule may contain usually 5–20 mg of the active compound when the composition is orally administered. In case the composition is given parenterally, a unit dosage such as a vial may usually contain about 1–10 mg of the compound.

It will be understood that the actual dosage changes, as a matter of course, depend upon the conditions of individual patient and, therefore, it should be specifically determined when used. However, it will be safe and convenient if the dosage in terms of the active compound is usually 10–100 mg, preferably 10–60 mg per day for an adult when administered orally, and usually 1–100 mg, preferably 1–50 mg, per day for an adult in the case of the parenteral injection.

EXPERIMENT 1

The acute toxicity ($LD_{50}$) of the compound of Example 2 was determined by the use of SD strain male and female rats (4 weeks old) which were orally or intravenously administered the compound. $LD_{50}$ against both male and female rats ranged from 1,200 to 1,300 mg/kg for oral administration and from 800 to 1,000 mg/kg for intravenous administration.

EXPERIMENT 2

Adult mongrel dogs which had been anesthetized by the intravenous administration of 30-40 mg/kg of pentobarbital sodium were subjected to thoracotomy under oxygenic ventilation by use of Bird's respirator and thereafter various physical phenomena were measured in the following manner.

(1) Coronary blood flow (CBF)

An electromagnetic flowmeter probe was attached to a circumflex branch or an origin of an anterior descending branch of the left coronary artery.

(2) Coronary perfusion pressure (CBP)

The fire catheter connected to a pressure transducer was inserted into the distal side of the probe in the circumflex branch of the left coronary artery.

(3) Aortic blood flow (AoBF)

An electromagnetic flowmeter probe was attached to the origin of aorta.

(4) Left ventricular tension (LVT)

A strain gauge was sewn on the anterior wall of the left ventricle.

(5) Systemic blood pressure (SBP)

A catheter connected to a pressure transducer was inserted into the right femoral artery.

(6) Heart rate (HR)

Heart rate was measured by a cardiotachometer using pulse pressure as trigger pulse.

(7) Electrocardiogram (ECG)

An electrocardiogram was recorded according to an unipolar lead in the cardiac surface using different electrode set on a portion of anterior wall of left ventricle.

In addition to the test Items 1-7 above, some of the test animals were subjected to the measurement of renal blood flow (RBF) and femoral blood flow (FBF) by attaching an electromagnetic flowmeter probe to the left renal artery and the left femoral artery.

The test compound of Example 1 was dissolved in the physiological saline solution or in the distilled water and administered intravenously, orally or sublingually, Nitroglycerin was administered in the same manner as an active control drug to compare with the test compound.

Results (I) Intravenous Administration (a) Change in coronary blood flow

Diastolic coronary flow began to increase 10-20 seconds after the intravenous administration of the test compound with a dose of 10 μg/kg or more. Systolic coronary flow was increased with a dose of 250 μg/kg or more, accompanied by transient decrease just after the administration. Mean coronary flow showed a persistent increase after the administration of the test compound.

Figure 1:
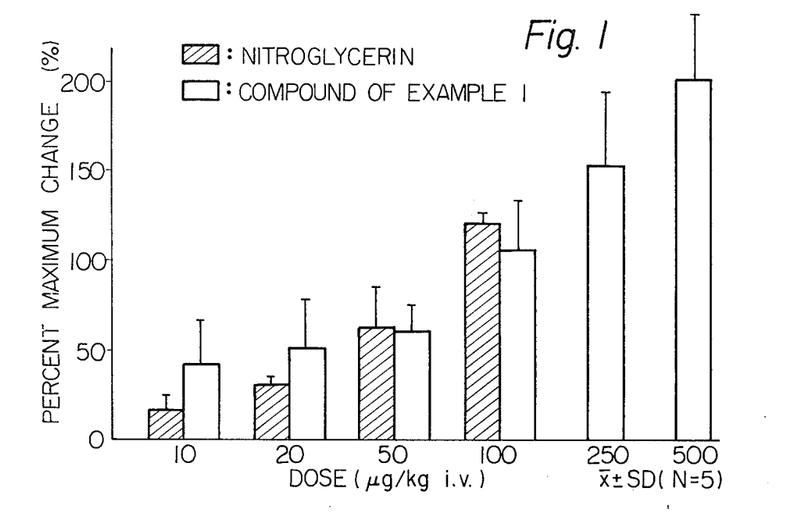
FIG. 1 is a graph showing percent increase in coronary blood flow when the compound prepared according to Example 1 or nitroglycerin was intravenously administered in accordance with Experiment 1.
Figure 2:
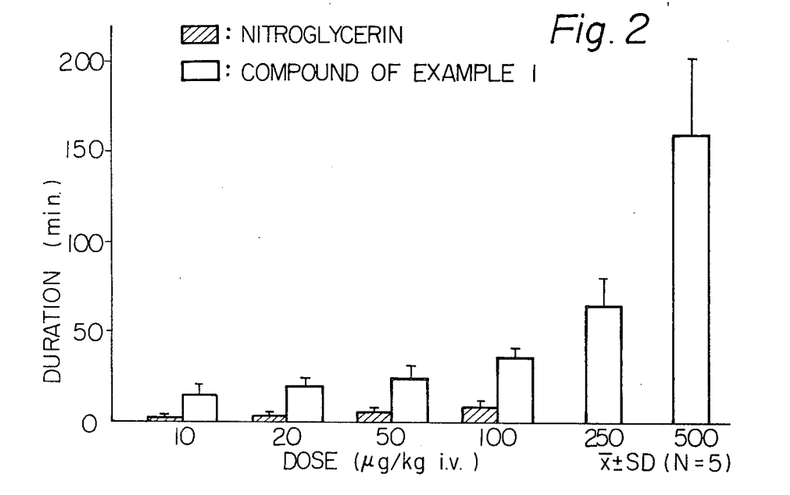
FIG. 2 is a graph showing the duration of increase in coronary blood flow when the compound of Example 1 or nitroglycerin was intravenously administered in accordance with Experiment 1.

The increasing degree of coronary flow is shown in FIGS. 1 and 2 in terms of maximum percent change and duration against the values before administration.

The administration of the compound of this invention even in a dose level of 10 μg/kg i.v. produced a significant increase in coronary flow and in a dose level of 500 μg/kg i.v. caused an increase so remarkable as to appear to be reactive hyperemia. In the latter case, the duration of increase in coronary flow approached 3 hours. The effect of the compound of this invention was superior to that of nitroglycerin, particularly in the duration of action.

(b) Change in left ventricular tension

Figure 3:
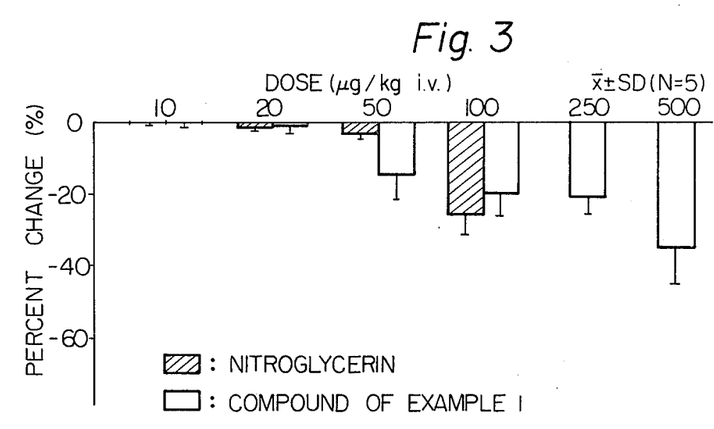
FIG. 3 is a graph showing the change in the left ventricular tension when the compound of Example 1 or nitroglycerin was intravenously administered in accordance with Experiment 1.

As shown in FIG. 3, the left ventricular tension caused a slight decrease after the intravenous administration of the compound of Example 1 in a dose level of 50 μg/kg or more. The decrease was almost equivalent to that of nitroglycerin in the tested dose range. However, the maximum percent decrease was 33% or less even in a dose level of 500 μg/kg i.v.

(c) Change in heart rate

Figure 4:
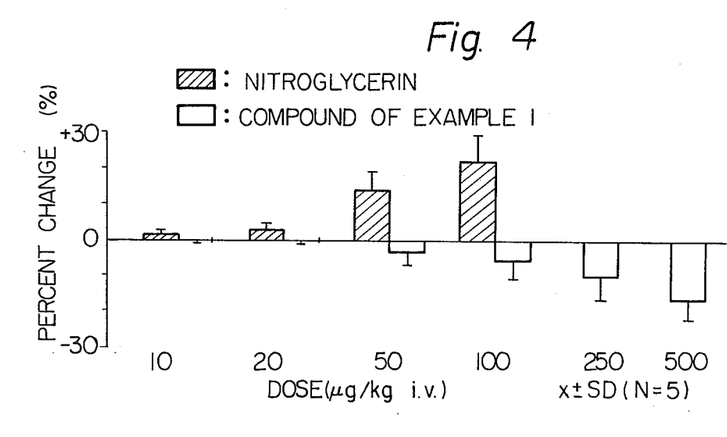
FIG. 4 is a graph showing the change in heart rate when the compound of Example 1 or nitroglycerin was intravenously administered in accordance with Experiment 1.

As shown in FIG. 4, the heart rate showed almost no change by the administration of the compound of this invention in a dose level up to 20 μg/kg i.v., while, in a dose level of 50 μg/kg i.v. or more, presented a slight dose-dependent decrease to reach 17% in a dose level of 500 μg/kg i.v. In contrast, the administration of nitroglycerin in a dose level of more than 10 μg/kg i.v. increased the heart rate.

(d) Change in electrocardiogram

Figure 5:
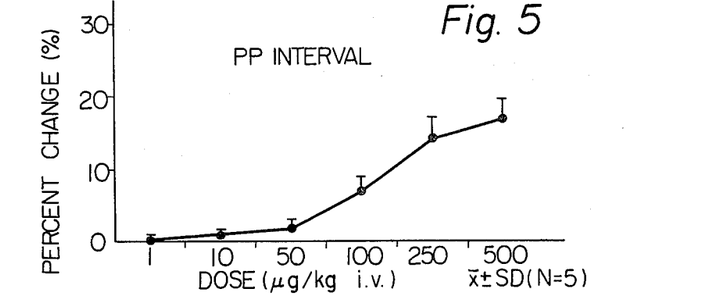
FIGS. 5, 6 and 7 are graphs showing the change in electrocardiograms when the compound of Example 1 was intravenously administered.
Figure 6:
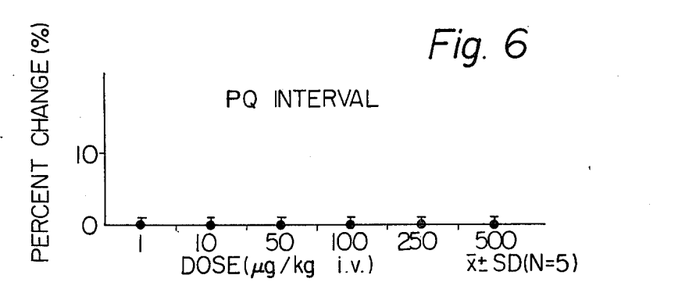
Figure 7:
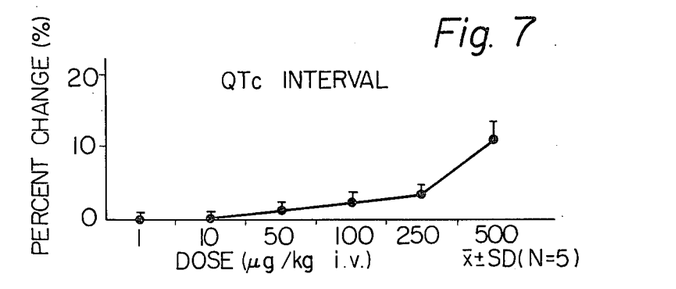

As shown in FIGS. 5 and 7, PP and QTc intervals were prolonged dose-dependently by the intravenous administration of the compound of Example 1 with a dose more than 50 μg/kg, while the PQ interval (FIG. 6) had almost no change by the administration of dose up to 1,000 μg/kg i.v.

(e) Change in systemic blood pressure

Figure 8:
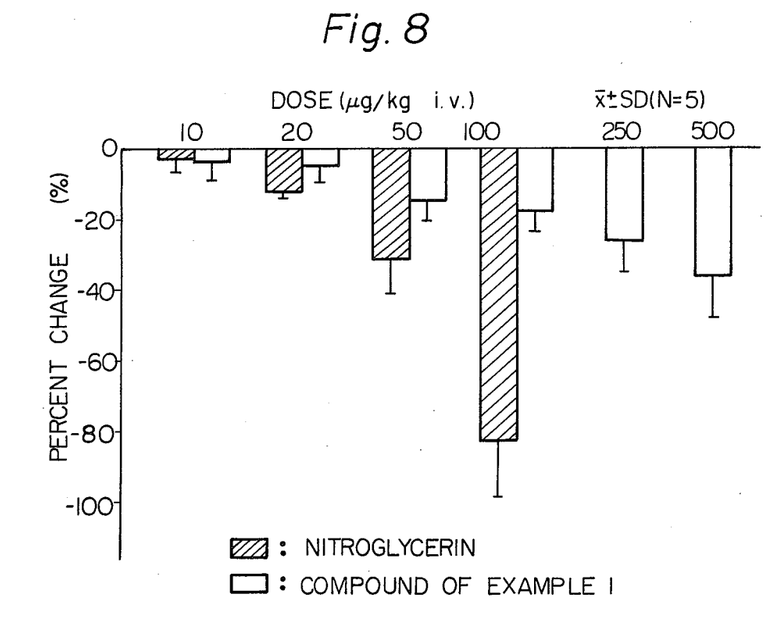
FIG. 8 is a graph showing the change in systemic blood pressure when the compound of Example 1 or nitroglycerin was intravenously administered in accordance with Experiment 1.
Figure 9:
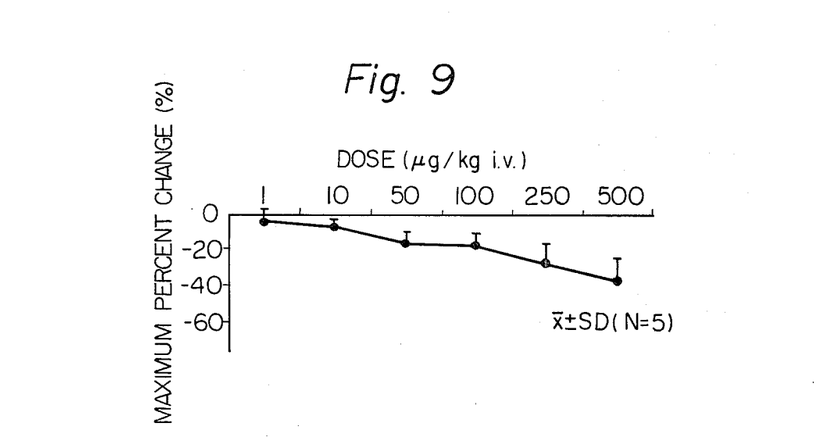
FIGS. 9 and 10 are graphs showing the change in systemic blood pressure when the compound of Example 1 was intravenously administered according to Experiment 1.
Figure 10:
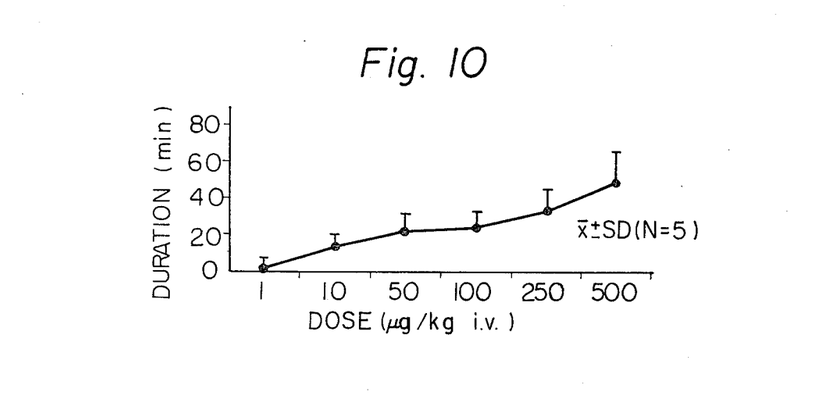

As shown in FIGS. 8, 9 and 10, the systemic blood pressure presented a significant, dose-dependent fall by the intravenous administration of the test compound in a dose level of more than 50 μg/kg. The effect of the compound on blood pressure was not stronger than that of nitroglycerin, but the duration was longer than that produced with nitroglycerin.

(f) Change in aortic blood flow

Figure 11:
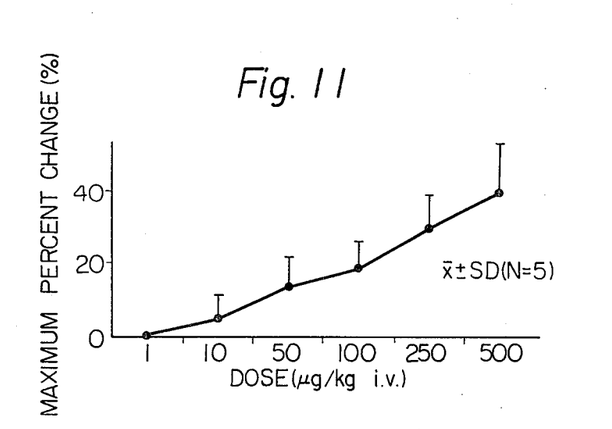
FIGS. 11 and 12 are graphs showing the change in aortic blood flow when the compound of Example 1 was intravenously administered.
Figure 12:
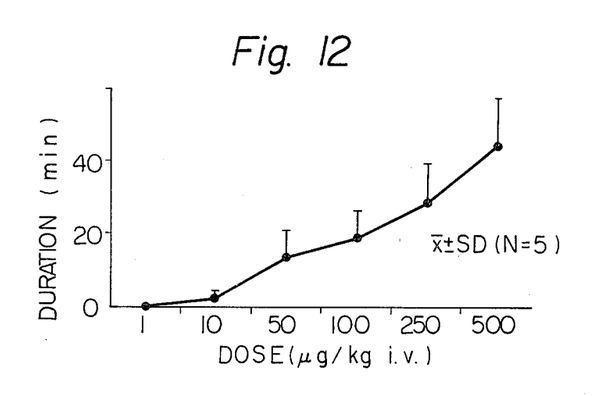

As shown in FIGS. 11 and 12, the aortic blood flow presented a slight, dose-dependent increase by the intravenous administration of the compound of Example 1 in a dose level of 10 μg/kg or more. The percent increase in a dose level of 500 μg/kg i.v. reached maximum 40%, but the duration was not so long in comparison with the degree of increase in coronary flow.

(g) Change in renal or femoral flow

The renal and femoral flows were increased in spite of a fall in systemic blood pressure by the intravenous administration of the compound of Example 1 in a dose level of 100 to 250 µg/kg. However, the increase in the renal and femoral flows were less than that in coronary flow concerning the degree and the duration.

From the test results stated above, it was confirmed that the compound of this invention had an increasing effect on coronary flow far superior to that of nitroglycerin and, in addition, it produced a fall in blood pressure, a decrease in heart rate and a reduction in cardiac tension, which were not excessive even in a high dose level.

Moreover, the fact that the compound of this invention did not disturb the conduction of excitation in the heart as shown in no prolonged PQ interval of electrocardiogram, indicates that it may be very useful as a drug for ischemic heart disease.

The compound could be used as an antihypertensive drug or a peripheral vasodilator because it has a long-lasting and mild antihypertensive action and a dilating action for femoral and renal vessels, as well as a desirable effect on ischemic heart.

(II) Oral and Sublingual Administration

The compound prepared according to Example 2 was sublingually administered to dogs as a tablet containing 1–10 mg of the compound. About 2 minutes after the administration, coronary flow was apparently increased. The compound in a dose level of 10 mg showed almost no change in systemic blood pressure, cardiac tension and aortic flow. In contrast, the sublingual administration of a tablet containing the hydrochloride of the active compound did not show any subtantial increase in coronary flow. When the compound prepared according to Example 1 or 2 in either its free form or hydrochloride was intraduodenally administered in a dose level of 50 µg/kg or more, an apparent, longlasting increase in coronary flow was observed.

From the test results, the compound of this invention may be used as various preparations, such as for parenteral injection; or in the form of capsule, tablet, granule or powder for oral administration or in sublingually administrative form. In contrast, nitroglycerin is not absorbed through the intestinal wall and, therefore, only sublingual administration is available.

EXPERIMENT 3

Adult mongrel dogs which had been anesthetized by the intravenous administration of 30–40 mg/kg of pentobarbital sodium were subjected to thoracotomy under oxygenic ventilation by the use of Bird's respitator. A catheter was inserted towards a proximal direction into a branch of an origin of the left coronary artery and a contrast media such as Conlaxin H ® or Angioconrei ® was injected through the catheter. The morphological change in the left coronary artery was filmed using a 35 mm cinefilm before and after the injection of the compound. From the analysis, it was found that the coronary artery was remarkably dilated by the intravenous administration of the compound of this invention in a dose level of 100 µg/kg or more.

EXPERIMENT 4

The same preparation as in Experiment 2 was set up using adult mongrel dogs anesthetized by the intravenous administration of pentobarbital sodium. The left anterior descending branch or circumflex branch of the coronary artery was mechanically strictured or occluded in the distal side of the portion attaching the electromagnetic flowmeter probe to experimentally induce cardiac ischemic phemonemon, and then the effect of the compound of Example 1 on the phenomenon was observed.

Under incomplete stricture, the coronary flow was slightly increased when the compound of Example 1 was intravenously administered in a dose level of 100 µg/kg or less, while slightly decreased when administered in a dose level of more than 250 µg/kg. After the administration of the compound of this invention, ST elevation of the electrocardiogram in the cardiac ischemic portion was apparently improved and, at the same time, the recovery of ventricular tension in an ischemic part was also observed. Under complete occlusion, the compound did not improve ST elevation or venticular tension in the midpoint of the ischemic portion, but the improvement in the surrounding point of the ischemic portion was recognized.

Similarly, when a tablet containing 10 mg of the free form of the compound prepared in Example 2 was sublingually administered, the coronary flow was increased and ST elevation in the electrocardiogram and a reduction in venticular tension were improved.

EXPERIMENT 5

(I) A papillary muscle isolated from a guinea pig was set in the organ bath filled with the oxygenized Tyrode's solution (Ca: 1.8 mM, K: 2.7 mM) at 30° C. One end of the muscle was fixed to the organ bath and the other end was connected to a tension meter by a thread. The effect of the compound of Example 1 on the muscle contraction force was observed by giving electric stimulation (20 V, 5 msec, 1 Hz) to the muscle with an Ag-AgCl electrode. The antagonistic action of the compound against calcium ion or isoproterenol was also investigated.

From the test results, it was found that the contraction of the papillary muscle induced by the electric stimulation was inhibited with the application of the compound of this invention in a concentration level of more than 1 µg/ml and that calcium ion had antagonistic effect against such inhibitory action. On the other hand, when isoproterenol was applied in a concentration level of 0.08 µg/ml, the papillary muscle exhibited excessive excitement to produce two or more irregular contractions per single electric stimulation. Under this state, the addition of the compound of this invention to the solution in a concentration level of more than 2 µg/ml inhibited the excessive excitement.

(II) A spiral strip isolated from the dog coronary artery was set in the organ bath filled with a $Ca^{++}$-free Lock's solution. One end of the strip was fixed to the organ bath and the other end was connected to a tension meter. The effect of the compound of Example 1 on the contraction of the strip induced by the polarization of the solution with the addition of 43 mM of $K^+$ and 1 mM of $Ca^{++}$ was investigated.

The test results showed that the contraction induced by $K^+$ depolarization was inhibited by the compound of this invention and such inhibitary action was diminished by the addition of $Ca^{++}$.

(III) The effect of $Ca^{++}$ on the increase in coronary flow was investigated using the dog anesthetized with pentobarbital sodium according to the same procedure as in Experiment 2-(I). The increase in coronary flow induced by the administration of the compound of this invention was inhibited by a larger dose of $Ca^{++}$.

(IV) Taenia coli of a guinea pig was suspended in the organ bath filled with Tyrode's solution and the effect of the compound of Example 1 on the spontaneous contraction and the contraction induced by K+ depolarization was investigated.

The test results showed that the spontaneous contraction and the K+ depolarization induced contraction were inhibited by application of the compound in a concentration level of 2 μg/ml and such inhibitary action was diminished by the addition of Ca++.

Analysis of the test results indicates that the compound of the present invention has an antagonistic action to Ca++, so that the inhibitory action to cardiac contraction the dilating action to smooth muscle of dog coronary artery and the inhibitory action to contraction of taenia coli of guinea pig induced by the application of the compound were antagonized by the addition of Ca++. Further, it was also found that the compound of this invention has an antiarrhythmic action because the compound inhibited the excessive excitement of papillary muscle induced by the administration of isoproterenol.

EXPERIMENT 6

The blood flow was made insufficient by loading experimentally the coronary artery of a dog, for example, by stricturing the coronary artery for a certain period of time, and the artery was allowed to sustain in this condition. According to this treatment, its peripheral blood pressure and peripheral blood flow repeated periodical and spontaneous fluctuations within minutes order period accompanied with ST elevation in electrocardiogram. This phenomenon was closely similar to the fit of variant angina pectoris in a clinical case. The periodical fluctuation has been proved to be caused by the periodical spasmus in the strictured coronary artery. The effect of the compound on such a variant angina pectoris model was investigated.

The test results show that the periodical fluctuations in the coronary blood pressure and coronary flow was inhibited by the intravenous administration of the compound of Example 1 in a dose level of 250 μg/kg or more. That is, the periodical fluctuation in blood flow apparently reduced, and only fine fluctuations remained. The effective duration of the inhibitory action ranged from 25 to 40 minutes.

As stated above, the compound of this invention is believed to be effective on the treatment of variant angina pectoris.

EXPERIMENT 7

According to the procedure explained below, the compound of Example 1 was subjected to investigate as to whether or not it has an anticoagulative action to platelets, namely antiembolic action.

1. Preparation of the test solution

1—1 Adjustment of platelet-rich plasma (PRP solution)

A rabbit blood containing 38% sodium citrate (blood: sodium citrate aqueous solution=9:1) was subjected to the centrifugation at 1,000 r.p.m. for 10 minutes, and the supernatant fluid was used as PRP solution.

1-2 Adjustment of an adenosine diphosphate solution (ADP solution)

Adenosine diphosphate (Sigma Chemical Co., Ltd.) was dissolved in a physiological saline solution at a concentration of 100 μg/ml.

1-3 Adjustment of collagen suspension

Fifty mg of collagen obtained from bovine tendon (Sigma Chemical Co., Ltd.) was suspended in 5 ml of a physiological saline solution and homogenized by a glassy homogenizer for 5 minutes. Next, it was subjected to centrifugation at 500 r.p.m. for 5 minutes, and the supernatant fluid was used as a collagen suspension.

1-4 The compound of Example 1 was dissolved in the physiological saline solution to obtain the test solution.

2. Method of measurement

The measurement was performed by the use of Aggregometer (Evans Electroselenium Ltd., Model 169).

PRP solution (0.5 ml) and the test solution (0.025 ml) or a physiological saline solution as the control (0.025 ml) were charged into two cuvettes, respectively, and then subjected to incubation at 37° C. for 2 minutes. Further, after 0.025 ml of ADP solution or 0.025 ml of the collagen suspension was added to each cuvette, the effect of the compound on platelet aggregation induced by ADP or collagen was measured.

Figure 13:
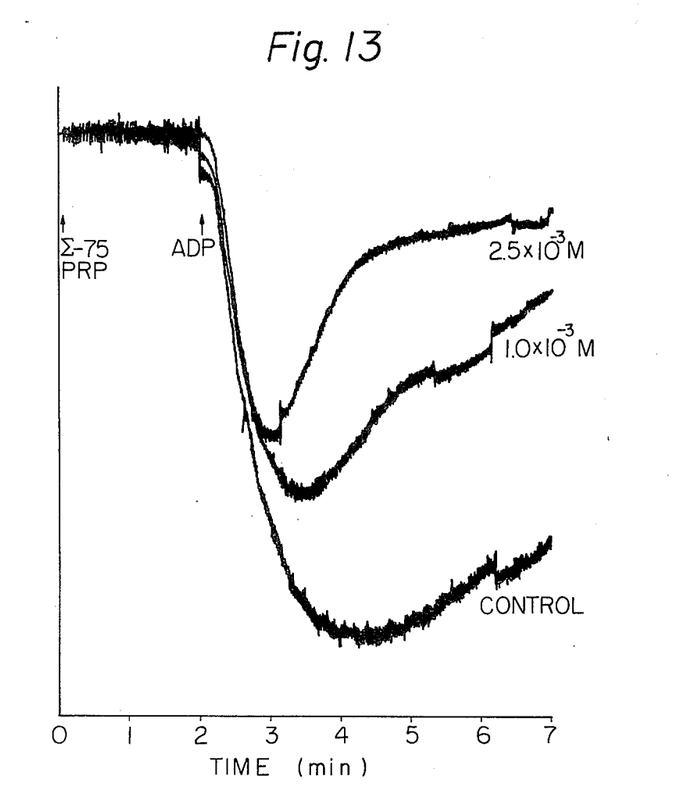
FIG. 13 is a test chart showing the effect of the compound of Example 1 to the platelet coagulation caused by adenosine diphosphate in accordance with Experiment 7.
Figure 14:
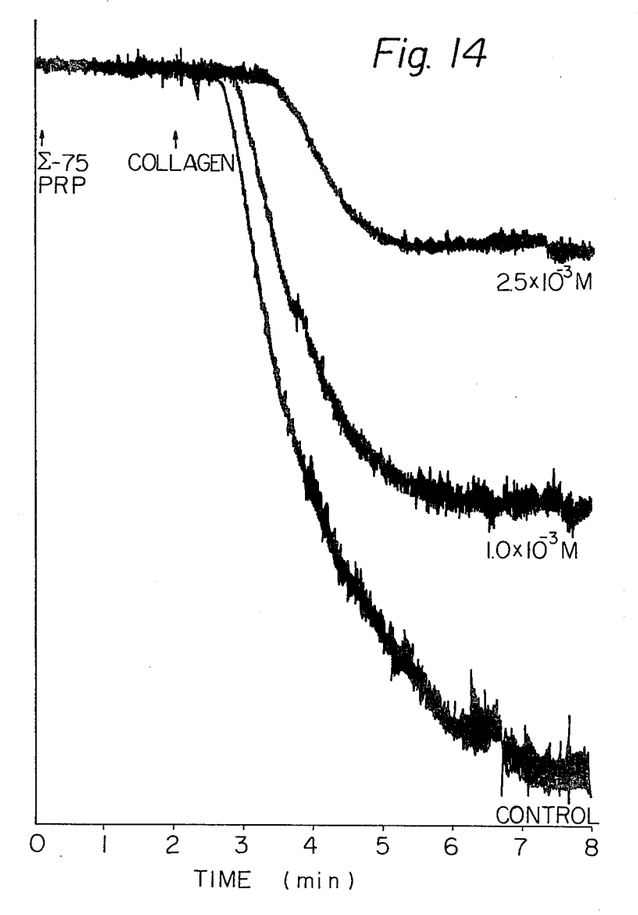
FIG. 14 is a test chart showing the effect of the compound to the platelet coagulation caused by collagen in accordance with Experiment 7.

As shown in FIGS. 13 and 14, the initial rate of ADP-induced aggregation in the test compound was the same as that in the control, but the test compound accelerated the dissociation of the aggregated platelets. On the other hand, the test compound delayed the onset of the collagen-induced aggregation and made a maximum extent of the aggregation lower than the control. From these results, the inhibitory effect of the compound on the platelet aggregation was confirmed, so that the compound of this invention was also found to be useful as an anticoagulant.

EXPERIMENT 8

By the same method as disclosed in Experiment 2, item 5, change in systemic blood pressure when test compounds were intravenously administered was measured. The results obtained are shown in the following Table.

Table

| Test Compound | Dose (μg/kg) | Percent Change of S.B.P. (%) | Duration (min.) |
|---|---|---|---|
| Compound of Example 1 | 50 | 16 | 22 |
| Nitric ester of N-(2-hydroxyethyl picolinamide | 50 | 20 | 17 |
| Nitroglycerin | 50 | 45 | 8 |

EXPERIMENT 9

In accordance with the methods of Experiment 2, Items 1, 5 and 6—except that beagle dogs which had been anesthetized by the intravenous administration of 30-40 mg/kg of pentobarbital sodium were used as test animals—the change of coronary blood flow (CBF), systemic blood pressure (SBP) and heart rate were measured upon administering the compound of Example 2, i.e. nitric ester of N-(2-hydroxyethyl) nicotinamide or the compound of Example 8 of U.S. Pat. No. 3,036,074, i.e. nitrate of the acid dinitroxydiethyl amide nicotinate. Further, in accordance with the methods disclosed in Experiments 4 and 6, the effects of both compounds upon the change of coronary blood flow under stricturing of the coronary artery and upon the variant angina pectoris model were measured.

Figure 15:
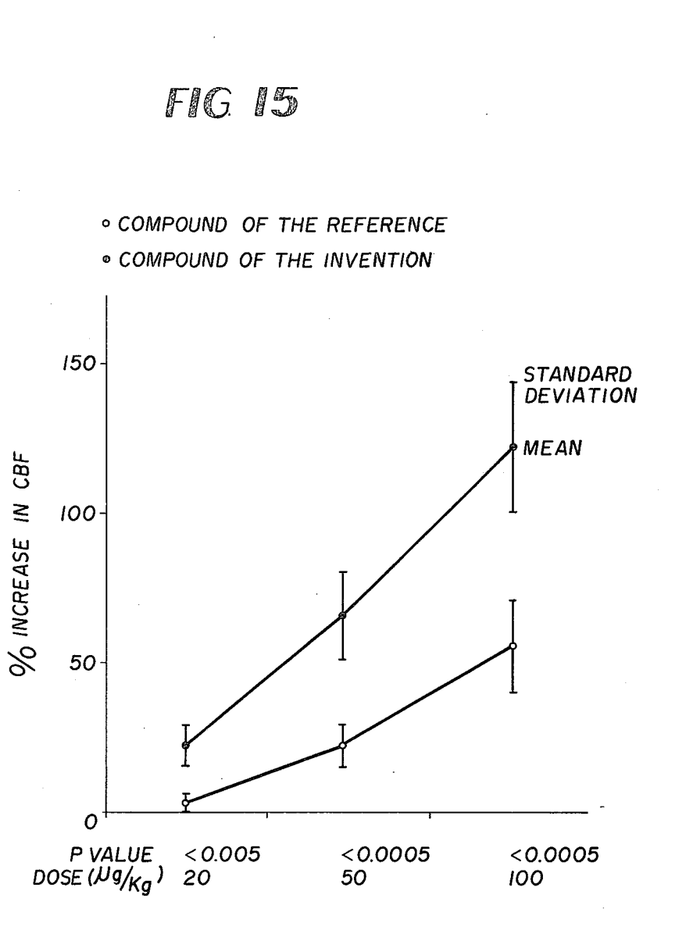
FIGS. 15-19 are comparison graphs showing the relative properties of the compound of Example 2 of the present invention compared with the compound of Example 8 of U.S. Pat. No. 3,036,074.
Figure 16:
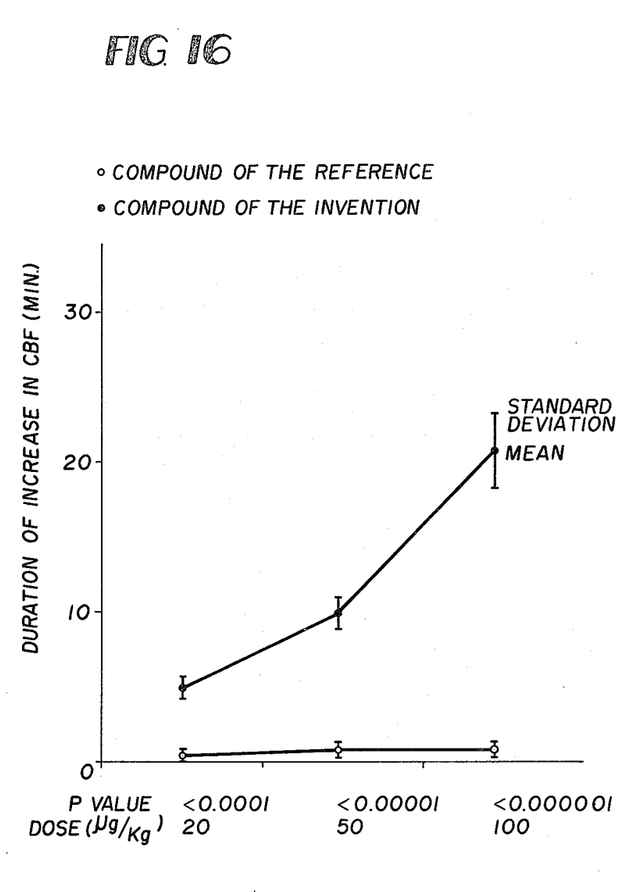

Results (a) Change in coronary blood flow (CBF):

The increase in CBF and the duration of increase in CBF by the administration of the compounds of Example 2 and of the reference patent are shown in FIG. 15 and FIG. 16, respectively.

The intravenous administration of the compound of Example 2 even in a dose of 20 μg/kg showed a significant increase in coronary flow. Further, the effect of such compound on the increase in coronary blood flow was significantly superior to the effect of the compound of Example 8 of U.S. Pat. No. 3,036,074 with respect to each different dose.

Similarly, the intravenous administration of the compound of Example 2 in a dose of 100 μg/kg showed a duration of action of over 20 minutes, while the duration of action given by the intravenous administration of the compound of the prior art is remarkably short. Thus, the difference in their action are significant.

Figure 17:
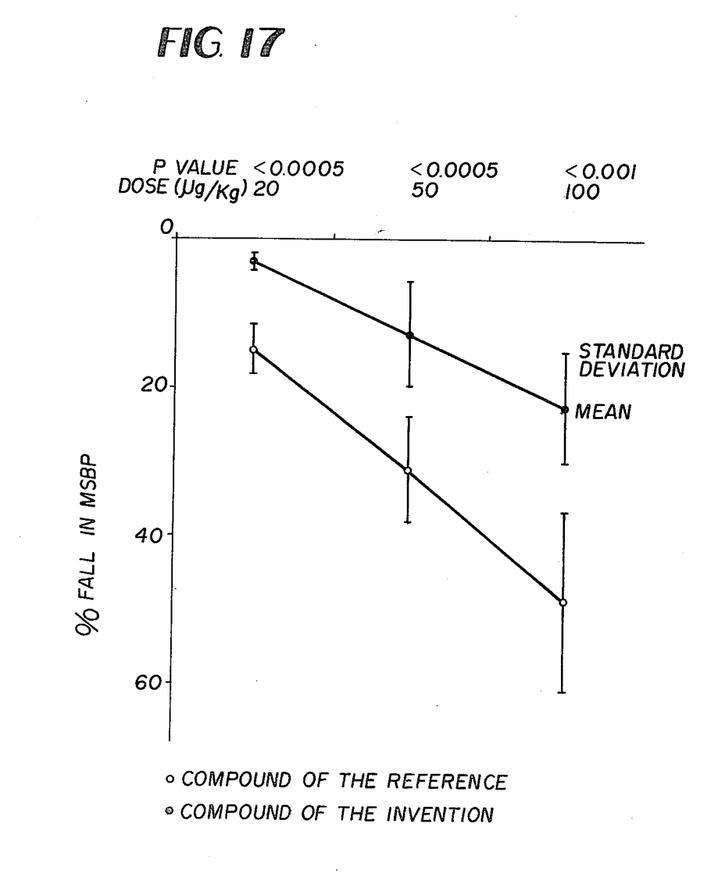

(b) Change in systemic blood pressure (SBP):

As shown in FIG. 17, the degree of drop of the systemic blood pressure induced by the administration of the compound of Example 2 was lower than that of the compound of the U.S. Pat. No. 3,036,074.

Figure 18:
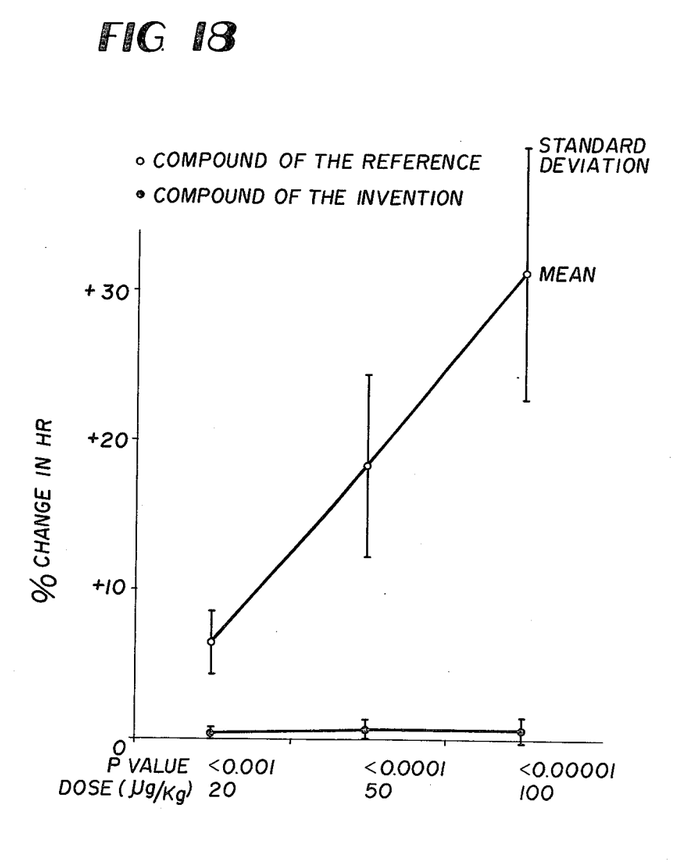

(c) Change in heart rate (HR):

As shown in FIG. 18, the heart rate showed almost no change by the administration of the compound of Example 2 while it was remarkably increased by the administration of the compound of U.S. Pat. No. 3,036,074.

Figure 19:
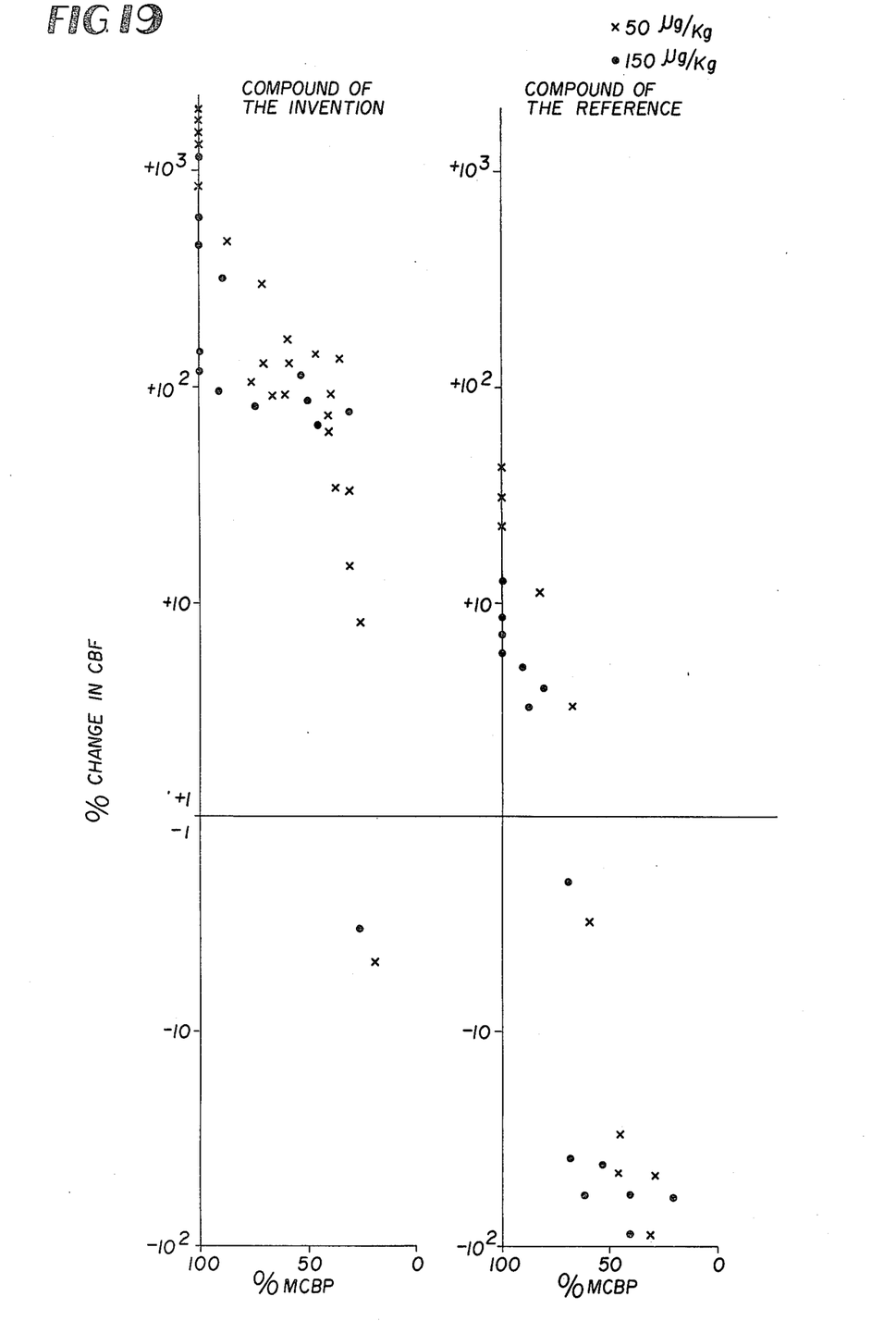

(d) Change in coronary blood flow under stricturing of coronary artery:

As shown in FIG. 19, coronary flow showed an increase by the intravenous administration of the compound of Example 2, but, in contrast, it showed a drop by the administration of the compound of U.S. Pat. No. 3,036,074.

(e) Effects of the compound on variant angina pectoris:

The intravenous administration of the compound of Example 2 in a dose of more than 150 μg/kg had an inhibiting effect on abnormal change in electrocardiogram (ST-elevation) and on the periodical fluctuation in the coronary blood flow. In contrast, the intravenous administration of the compound of Example 8 of U.S. Pat. No. 3,036,074 even in a dose of 300 μg/kg showed no such inhibiting effect.

In general, the pharmacological activities required as an anti-anginal drug which is the subject of this invention are to increase the coronary blood flow over a prolonged period of time without significantly changing the heart rate and blood pressure. From these viewpoints, the compound of this invention is, as shown in the above test results, far superior in the activity required for an anti-anginal drug to the compound disclosed in Example 8 of U.S. Pat. No. 3,036,074.

Further, in the tests using pathological models, particularly in the test using a variant angina pectoris model by stricturing the coronary artery, the compound of this invention showed excellent effects although no significant effects were seen with use of the compound of Example 8 of U.S. Pat. No. 3,036,074.

EXAMPLE 1

To a mixture of 5 g of sodium hydrogen carbonate, 15 ml of water, 1.69 g of the nitric ester of monoethanolamine nitrate and 20 ml of chloroform was added slowly 2.5 g of nicotinyl chloride hydrochloride over 10 to 30 minutes under stirring at 0° to 5° C. The stirring was continued for an additional 30 minutes and then the chloroform layer was separated. The remained aqueous layer was extracted with chloroform and the extract was combined with the separated chloroform layer. The organic layer was washed with a potassium carbonate aqueous solution, dried over anhydrous sodium sulfate and evaporated under reduced pressure to dryness. The residue was dissolved in ether-isopropanol (1:1) and then hydrogen chloride was bubbled into the solution under cooling to give 2.35 g of the nitric ester of N-(2-hydroxyethyl) nicotinamide hydrochloride. Recrystallization from ethanol afforded colorless needle crystals having a melting point of 132° C.

Analysis: Calcd. for $C_8H_{10}N_3O_4Cl$: C, 38.80; H, 4.07; N, 16.96 (%). Found: C, 38.89; H, 4.02; N, 16.72 (%).

IR(cm$^{-1}$): NH, 3255; C=O, 1669; ONO$_2$, 1640.

EXAMPLE 2

To a solution of 1.69 g of the nitric ester of monoethanolamine in 20 ml of pyridine was added slowly 2.5 g of nicotinyl chloride hydrochloride over 10 to 30 minutes after stirring at 5° C. After stirring for an additional 30 minutes, the reaction mixture was evaporated to dryness. The residue was dissolved in chloroform and the solution was washed with a sodium hydrogen carbonate aqueous solution. The organic layer was separated, dried over anhydrous sodium sulfate and evaporated under reduced pressure to dryness. The residue was chromatographed on silica gel (Wakogel C-200; Wako Pure Chemical Industries, Ltd., Japan) and eluted with benzene-ethanol (5:1). The eluent was evaporated to a semi-solid mass which was crystallized from diethyl ether to give 1.97 g of the nitric ester of N-(2-hydroxyethyl) nicotinamide.

Recrystallization of the crystals from diethyl ether-ethanol afforded colorless needles having a melting point of 92° to 93° C.

EXAMPLE 3

A solution of 10 g of the nitric ester of N-(2-hydroxyethyl) nicotinamide hydrochloride in water was neutralized with a sodium hydrogen carbonate aqueous solution. The solution was extracted with chloroform and the extract was dried over anhydrous sodium sulfate and evaporated under reduced pressure to dryness. The residue was crystallized from diethyl ether to give 7 g of the nitric ester of N-(2-hydroxyethyl) nicotinamide. Recrystallization from isopropanol-diethyl ether gave colorless needles having a melting point of 93° C.

IR (cm$^{-1}$): NH, 3250, ONO$_2$, 1630

EXAMPLE 4

To a mixture of 1.69 g of the nitric ester of monoethanolamine nitrate in 5 ml of water, 3.8 ml of 35% potassium carbonate solution and 17 ml of tetrahydrofuran were added alternately 3 g of isonicotinyl chloride hydrochloride and 11.2 ml of 35% potassium carbonate aqueous solution over 30 minutes under stirring at 0° to 5° C. The reaction mixture was stirred for an additional 15 minutes, and the organic layer was separated. The aqueous layer was extracted with tetrahydrofuran and the extract was combined with the previously separated organic layer. The combined organic layers were dried over anhydrous sodium sulfate and filtered. Evaporation of the solvent in vacuo and crystallization of the residue afforded the nitric ester of N-(2-hydroxyethyl) isonicotinamide.

The product was dissolved in diethyl ether and the dropwise addition of diethyl ether-fuming nitric acid under cooling gave 1.5 g of the nitric ester of N-(2-hydroxy-ethyl) isonicotinamide nitrate. Recrystallization from isopropanol afforded the crystals having a melting point of 105° C. (decomposition).

Analysis: Calcd. for $C_8H_{10}N_4O_7$: C, 35.04; H, 3.68; N, 20.43 (%). Found: C, 35.00; H, 3.59; N, 20.38 (%).

IR(cm$^{-1}$): NH, 3280; C=O, 1671; $ONO_2$, 1625.

EXAMPLE 5

N-(2-hydroxyethyl) nicotinamide nitrate (1.145 g) was gradually added to 3 ml of fuming nitric acid which had been cooled to a temperature of from $-10°$ to $-5°$ C. while stirring. After stirring for an additional one hour at 0°–5° C., diethyl ether was added to the solution to precipitate 1.15 g of nitric ester of N-(2-hydroxyethyl) nicotinamide nitric acid ester as colorless crystals. The crystals were dissolved in a sodium carbonate aqueous solution and ethyl acetate was added to the solution. The ethyl acetate layer was separated, dried over sodium sulfate and evaporated under reduced pressure. The residue was crystallized from diethyl ether to give nitric ester of N-(2-hydroxyethyl) nicotinamide. Recrystallization from diethyl ether afforded colorless crystals having a melting point of 90°–92° C.

Analysis: Calcd. for $C_8H_9N_3O_4$: C, 45.50; H, 4.29; N, 19.89 (%). Found: C, 45.37; H, 4.09; H, 19.71 (%).

EXAMPLE 6

By the procedure similar to that of Example 5, N-(2-hydroxyethyl) isonicotinamide nitrate was reacted with fuming nitric acid to obtain nitric ester of N-(2-hydroxy-ethyl) isonicotinamide nitrate. (Yield: 76%, mp: 105° C. (decomposition))

Analysis: Calcd. for $C_8H_{10}N_4O_7$: C, 35.04; H, 3.68; N, 20.43 (%). Found: C, 35.11; H, 3.57; N, 20.34 (%).

EXAMPLE 7 (Pharmaceutical Preparation)

| (a) Sublingual Tablet | |
|---|---|
| Compound prepared according to Example 2 | 5 mg |
| Lactose | 19.7 mg |
| Mannitol | 25 mg |
| Magnesium Stearate | 0.3 mg |
| Total | 50 mg/tablet |

The ingredients were uniformly blended in the proportions described above and the mixture was formed into tablets, each tablet being 5 mm in diameter and 50 mg in weight.

| (b) Tablet for Internal Use | |
|---|---|
| Compound prepared according to Example 1 | 10 mg |
| Lactose | 44.5 mg |
| Corn Starch | 20 mg |
| Crystalline Cellulose | 25 mg |
| Magnesium Stearate | 0.5 mg |
| Total | 100 mg/tablet |

The ingredients were uniformly blended in the proportions described above and the mixture was formed into tablets, each tablet being 7 mm in diameter and 100 mg in weight.

| (c) Hard Capsules | |
|---|---|
| Compound prepared according to Example 2 | 20 mg |
| Lactose | 176 mg |
| Magnesium Stearate | 4 mg |
| Total | 200 mg/capsule |

The ingredients were uniformly blended in the proportions described above and hard capsules each being identified as No. 3 were filled with 200 mg each of the mixture by a packing machine to form capsules each weighing 250 mg.

| (d) Granules | |
|---|---|
| Compound prepared according to Example 2 | 10 mg |
| Lactose | 12 710 mg |
| Paste of Cornstarch | 280 mg |
| Total | 1,000 mg/wrapper |

The ingredients were uniformly kneaded and then granulated to form granules, each granule having a diameter of about 1 mm.

| (e) Parenteral Injection | |
|---|---|
| Compound prepared according to Example 2 | 5 mg |
| Mannitol | 50 mg |
| Total | 55 mg/vial |

The ingredients were dissolved in 1 ml of distilled water and the solution was sterilized and filtered. The solution was filled in a vial and freeze-dried and the vial was sealed to form a parenteral injection. The freeze-dried mixture was dissolved in 1 ml of distilled water when it is used as parenteral injection.

It will be obvious to those skilled in the art that various changes may be made without departing from the scope of the invention and the invention is not to be considered limited to what is shown in the drawings and described in the specification.

What is claimed is:

1. Nitric ester of N-(2-hydroxyethyl) nicotinamide or a pharmaceutically acceptable salt thereof.

2. Nitric ester of N-(2-hydroxyethyl) nicotinamide acid addition salt according to claim 1, selected from the group consisting of the acid addition salts hydrochloride, nitrate, oxalate, p-toluenesulfonate and maleate.

3. Nitric ester of N-(2-hydroxyethyl) nicotinamide hydrochloride according to claim 1.

4. A pharmaceutical composition for treating circulatory disease which comprises a circulatory improving-effective amount of the nitric ester of N-(2-hydroxyethyl) nicotinamide or a pharmaceutically acceptable salt thereof, and a pharmaceutically acceptable carrier.

5. A pharmaceutical composition according to claim 4, wherein said composition is in an orally administrative form selected from tablet, granule, powder, capsule or suspension.

6. A pharmaceutical composition according to claim 4, wherein said carrier is selected from lactose, starch, kaolin, crystaline cellulose, talc, calcium carbonate or magnesium stearate.

7. A process for treating circulatory diseases comprising administration to a patient in need of such therapy a circulatory improving-effective amount of the compound of claim 1.

8. A process according to claim 7, wherein 10-100 mg per day are administered.

9. A process according to claim 8, wherein 10-60 mg per day are administered.

10. A process according to claim 7, wherein the compound is administered by parenteral injection.

11. A process according to claim 10, wherein 1-100 mg per day are administered.

12. A process according to claim 11, wherein 1-50 mg per day are administered.

13. A process according to claim 7, wherein said circulatory disease is ischemic heart disease.

14. A process according to claim 7, wherein said circulatory disease is hyperpiesia.

15. A process according to claim 7, wherein said circulatory disease is arrhythmia.

16. A process according to claim 7, wherein said circulatory disease is peripheral circulatory insufficiency.

17. A process according to claim 7, wherein said circulatory disease is thrombosis.

* * * * *